United States Patent [19]

Brechbuhler et al.

[11] 4,276,302
[45] Jun. 30, 1981

[54] MITICIDAL 2-(PHENOXY-ALPHA-ALKYL)-IMIDAZOLINES

[75] Inventors: Hans U. Brechbuhler, Basel; Günter Mattern, Liestal; Walter Traber, Reinach, all of Switzerland

[73] Assignee: Ciba-Geigy Corporation, Ardsley, N.Y.

[21] Appl. No.: 81,964

[22] Filed: Oct. 4, 1979

[30] Foreign Application Priority Data

Oct. 9, 1978 [CH] Switzerland ............... 10469/78

[51] Int. Cl.$^3$ ............... A01N 43/50; C07D 233/22
[52] U.S. Cl. ............... 424/273 R; 548/353
[58] Field of Search ............... 548/353; 424/273 R

[56] References Cited

U.S. PATENT DOCUMENTS

| | | | |
|---|---|---|---|
| 2,149,473 | 3/1939 | Sonn | 548/353 |
| 3,449,357 | 6/1969 | White | 548/353 |
| 3,639,603 | 2/1972 | Marshall | 548/353 X |
| 3,966,757 | 6/1976 | Baganz et al. | 548/353 |
| 4,146,647 | 3/1979 | Lafon | 548/353 X |
| 4,226,876 | 10/1980 | Copp et al. | 548/353 X |
| 4,232,011 | 11/1980 | Böger et al. | 548/353 X |

FOREIGN PATENT DOCUMENTS

| | | |
|---|---|---|
| 1935479 | 1/1971 | Fed. Rep. of Germany ........ 548/353 |
| 2756638 | 6/1978 | Fed. Rep. of Germany . |
| 51-106739 | 9/1976 | Japan . |
| 1181356 | 2/1970 | United Kingdom ............... 548/353 |

OTHER PUBLICATIONS

*Chemical Abstracts*, 70:68371x, (1969) [Baganz, H., et al., S. Africa, 68 00,850 7/2/68].
March; J., *Advanced Organic Chemistry*, McGraw-Hill, N.Y., 1968, p. 300.
Elderfield, R. (editor), *Heterocyclic Compounds*, vol. 5, John Wiley, N.Y., 1957, p. 239.

*Primary Examiner*—Richard A. Schwartz
*Attorney, Agent, or Firm*—Frederick H. Rabin; John J. Maitner

[57] ABSTRACT

Novel 2-(phenoxy-α-alkyl)-imidazolines of the formula

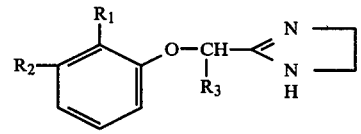

wherein $R_1$ and $R_2$, each independently of the other, are methyl or chlorine, or together they are —(CH$_2$)$_3$ or —(CH$_2$)$_4$ group and $R_3$ is ethyl, n-propyl or isopropyl, processes for obtaining these compounds and compositions containing them for the control of plant-damaging mites and mites which are parasites of animals.

17 Claims, No Drawings

MITICIDAL 2-(PHENOXY-ALPHA-ALKYL)-IMIDAZOLINES

The present invention relates to novel 2-(phenoxy-α-alkyl)-imidazolines, processes for their manufacture, and the use of these compounds as miticides in plant protection and for controlling mites which are parasites of animals.

The 2-(phenoxy-α-alkyl)-imidazolines of the invention have the formula I

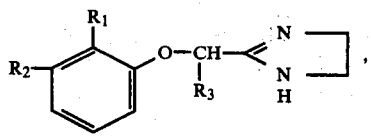

wherein $R_1$ and $R_2$, each independently of the other, are methyl or chlorine, or together are a $-(CH_2)_3-$ or $-(CH_2)_4-$ group, and $R_3$ is ethyl, n-propyl or isopropyl.

Compounds of formula I which have been found to be highly effective, in particular against plant-destructive mites, are those wherein $R_1$ and $R_2$, each independently of the other, are methyl or chlorine, and $R_3$ is ethyl or n-propyl.

The compounds of the present invention also comprise the addition salts of compounds of formula I with inorganic and organic acids. Preferred addition salts are those of inorganic acids, for example of hydrochloric acid, hydrobromic acid, hydriodic acid, sulfuric acid and nitric acid. Preferred addition salts of organic acids, are the oxalates, fumarates, tartrates and citrates. The preparation of these addition salts from compounds of formula I can be effected in conventional manner.

Differently substituted phenoxyalkylimidazolines are known as pharmaceutical active substances from German Offenlegungsschriften Nos. 1 695 555, 1 795 843 and 1 935 479. Further, substituted phenoxymethylimidazolines are proposed as agents for controlling arthropods in German Offenlegungsschriften Nos. 2 756 638 and 2 756 639. The compounds mentioned in these publications are chiefly suitable for controlling ectoparasitic representatives of the order Acarina, in particular ticks that are parasites of mammals.

It has now been found that the compounds of formula I and the acid addition salts thereof have a surprisingly potent and specific activity against plant-parasitic mites and mites which are parasites of animals. Thus the compounds of formula I can be employed for controlling phytophagous mites of the families Tetranychidae and Phytoptipalpidae (spider mites), Tarsonemidae (soft-bodied mites) and Eriophyidae (gall mites). The compounds of formula I are suitable in particular for controlling the following species of mites which infest crops of fruit and vegetables: *Tetranychus urticae, Tetranychus cinnabarinus, Panonychus ulmi, Bryobia rubrioculus, Panonychus citri, Eriophyes pyri, Eriophyes ribis, Eriophyes vitis, Tarsomemus pallidus, Phyllocoptes vitis* and *Phyllocuptura oleivora*. With the aid of compounds of formula I it is also possible to control parasitic mites of the families Sarcoptidae, Psoroptidae, Dermanyssidae and Demodicidae, in particular scab mites of the species *Sarcoptes scabiei* and *Notoedres cati*, which penetrate deep into the epidermis of domestic animals and productive livestock infested by them and cause severe irritation and damage, and also the species *Dermanyssus gallinae* and *Psoroptes ovis*.

The novel compounds of formula I can be obtained by methods which are known per se, for example by one of the following methods:

(a) reaction of an alkali metal salt of a phenol of the formula II

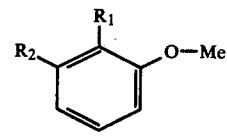

with a 2-(α-haloalkyl)-imidazoline hydrochloride of the formula III

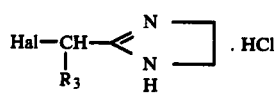

[cf. J. Amer. Chem. Soc. 69, 1688 (1947)];

(b) reaction of an imido ester of the formula IV

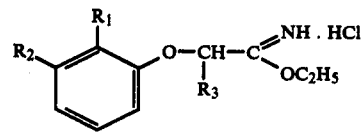

with ethylenediamine (op. cit., ibid.);

(c) reaction of a nitrile of the formula V

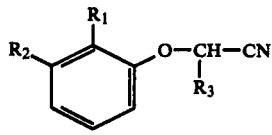

with ethylenediamine (op. cit., ibid.);

(d) reaction of an amidine salt of the formula VI

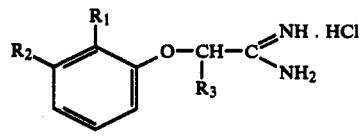

with ethylenediamine (op. cit., ibid.);

(e) reaction of a carboxylic acid ester of the formula VII

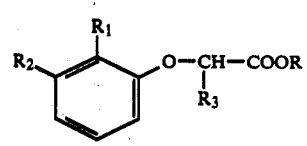

with ethylenediamine (op. cit., ibid.);

(f) reaction of a nitrile of the formula V with ethylenediamine and a sodium polysulfide containing 3 to 5 sulfur atoms (cf. German Offenlegungsschrift No. 2 512 513);

(g) reaction of a thioamide of the formula VIII

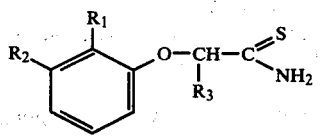

with ethylenediamine.

In the above formulae II, III, IV, V, VI, VII and VIII, the symbols $R_1$, $R_2$ and $R_3$ are as defined for formula I, Me is an alkali metal atom, preferably sodium, Hal is a halogen atom, preferably chlorine or bromine, and R is methyl or ethyl.

The starting materials employed in the above processes (a) to (g) are known or they can be obtained by methods which are known per se. Thus, for example, carboxylic acid esters of formula VII can be obtained by reaction of a lower alkyl ester of a haloacetic acid substituted in the α-position by the radical $R_3$ with a phenolate of formula II.

The corresponding reaction of a haloacetonitrile substituted in the α-position by the radical $R_3$ yields nitriles of the formula V. The further reaction of nitriles of the formula V with ethanol in the presence of hydrogen chloride yields hydrochlorides of imido esters of the formula IV, which can be converted with ammonia into amidines of the formula VI. Finally, 2-(α-haloalkyl)-imidazoline hydrochlorides of the formula III can be obtained by reaction of a haloacetimidoalkyl ester substituted by the radical $R_3$ with ethylenediamine (cf. Helv. Chimica Acta 27, 1762 (1944) and Swiss patent specification No. 229.606). Nitriles of the formula V can furthermore be obtained from carboxylic acid esters of the formula VII by reaction with ammonia and subsequent elimination of water to produce the corresponding amide. Thioamides of the formula VIII can be obtained by reaction of nitriles of the formula V with hydrogen sulfide.

The action of the compounds of the formula I and the compositions containing them can be substantially broadened and adapted to prevailing circumstances by addition of other insecticides and/or acaricides. Examples of suitable additives include: organophosphorus compounds, nitrophenols and derivatives thereof, formamidines, ureas, pyrethroids, carbamates and chlorinated hydrocarbons.

The compounds of formula I may be used as pure active substance or together with suitable carriers and/or adjuvants. Suitable carriers and adjuvants can be solid or liquid and correspond to the substances conventionally used in the art of formulation, for example natural or regenerated substances, solvents, dispersants, wetting agents, tackifiers, thickeners or binders.

For application, the compounds of the formula I may be processed to dusts, emulsifiable concentrates, granules, dispersions, sprays, to solutions, or suspensions, in the conventional formulation which is commonly employed in application technology. In addition, cattle dips and spray races, in which aqueous preparations are used, may also be mentioned. These formulations are particularly suitable for controlling pests which are parasites of animals.

The compositions of the present invention are prepared in known manner by homogeneously mixing and/or grinding active substances of formula I with the suitable carriers, with or without the addition of dispersants or solvents which are inert to the active substances.

The compounds of formula I may be processed to the following formulations:

Solid formulations: dusts, tracking powders and granules (coated granules, impregnated granules and homogeneous granules).

Liquid formulations:
(a) water-dispersible active substance concentrates: wettable powders, pastes and emulsions;
(b) solutions.

The content of active substance in the above described compositions is between 0.1% and 95%.

The compounds (active substances) of formula I can, for example, be formulated as follows (throughout the present specification all parts and percentages are by weight):

Dust

The following substances are used to formulate (a) a 5% and (b) 2% dust:
(a)
  5 parts of active substance,
  95 parts of talc;
(b)
  2 parts of active substance,
  1 part of highly disperse silicic acid,
  97 parts of talc.

The active substances are mixed and ground with the carriers.

Granules

The following substances are used to formulate 5% granules:
  5.00 parts of active substance,
  0.25 parts of epichlorohydrin,
  0.25 parts of cetyl polyglycol ether,
  3.50 parts of polyethylene glycol,
  91.00 parts of kaolin (particle size 0.3–0.8 mm).

The active substance is mixed with epichlorhydrin and the mixture is dissolved in 6 parts of acetone; the polyethylene glycol and cetyl polyglycol ether are then added. The resultant solution is sprayed on kaolin, and the acetone is subsequently evaporated in vacuo.

Wettable powders

The following constituents are used to formulate (a) a 40%, (b) and (c) a 25%, and (d) a 10% wettable powder:
(a)
  40 parts of active substance,
  5 parts of sodium dibutylnaphthalenesulfonate,
  54 parts of silicic acid;
(b)
  25.0 parts of active substance,
  4.5 parts of calcium ligninsulfonate,
  1.9 parts of Champagne chalk/hydroxyethyl cellulose mixture (1:1),
  1.5 parts of sodium dibutylnaphthalenesulfonate,
  19.1 parts of silicic acid,
  19.5 parts of Champagne chalk,
  28.1 parts of kaolin;
(c)
  25.0 parts of active substance,
  2.5 parts of isooctylphenoxy-polyoxyethyleneethanol,
  1.7 parts of Champagne chalk/hydroxyethyl cellulose mixture (1:1),
  8.3 parts of sodium aluminium silicate, 16.5 parts of kieselgur,
46.0 parts of kaolin;
(d)
10 parts of active substance,
3 parts of a mixture of the sodium salts of saturated fatty alcohol sulfates,
5 parts of naphthalenesulfonic acid/formaldehyde condensate,
82 parts of kaolin.

The active substances are homogeneously mixed with the additives in suitable mixers and the mixture is then ground in appropriate mills and rollers. Wettable powders are obtained which can be diluted with water to give suspensions of the desired concentration.

Emulsifiable concentrates

The following substances are used to formulate (a) a 10%, (b) a 25% and (c) a 50% emulsifiable concentrate:
(a)
10.0 parts of active substance
3.4 parts of epoxidised vegetable oil,
3.4 parts of a combination emulsifier consisting of fatty alcohol polyglycol ether and alkylarylsulfonate/calcium salt,
40.0 parts of dimethyl formamide,
43.2 parts of xylene;
(b)
25.0 parts of active substance
2.5 parts of epoxidised vegetable oil,
10.0 parts of alkylarylsulfonate/fatty alcohol polyglycol ether mixture,
5.0 parts of dimethyl formamide,
57.5 parts of xylene;
(c)
50.0 parts of active substance,
4.2 parts of tributylphenol-polyglycol ether,
5.8 parts of calcium dodecylbenzenesulfonate,
20.0 parts of cyclohexanene,
20.0 parts of xylene.

By diluting these concentrates with water it is possible to obtain emulsions of the required concentration.

Sprays

The following ingredients are used to formulate (a) a 5% spray, and (b) a 95% spray:
(a)
5 parts of active substance,
1 part of epichlorhydrin,
94 parts of ligroin (boiling range 160°–190° C.);
(b)
95 parts of active substance,
5 parts of epichlorhydrin.

The invention is further illustrated by the following Examples.

EXAMPLE 1: (Process e)

2-[α-(2,3-Dimethyl)-phenoxybutyl]-imidazoline 23.6 g of methyl 2-(2,3-dimethyl)-phenoxyvalerianate and 36 g of anhydrous ethylenediamine are dissolved in 60 ml of absolute methanol and the solution is refluxed for 20 hours. After the reaction mixture has cooled, the methanol is stripped off in vacuo and the crude product is stirred for 15 hours at 15 torr and 200° C. The still not completely solidified crude product is distilled, affording 2-[α-(2,3-dimethyl)-phenoxybutyl]-imidazoline with a boiling point of 118°–126° C./0.1 torr. On cooling to room temperature, the fraction melting at 82°–84° C. becomes solid.

Manufacture of the starting compound

A mixture of 42.7 g of 2,3-dimethylphenol, 68.3 g of methyl 2-bromovalerianate (b.p. 77°–80° C./17 torr), 70 g of anhydrous and finely ground potassium carbonate and 5 g of potassium iodide is boiled for 30 hours in 500 ml of methyl isobutyl ketone. The suspension is cooled and then filtered. The filtrate is concentrated, and the residue is taken up in ether. The ethereal solution is washed twice with dilute sodium hydroxide and then with water, dried over sodium sulfate, filtered and dried. 60 g of a dark oil are distilled. The fraction boiling at 102°–104° C./0.4 torr yields methyl 2-(2,3-dimethyl)-phenoxyvalerianate.

EXAMPLE 2

2-[α-(2,3-Dimethyl)-phenoxybutyl]-imidazoline hydrochloride 4 g of 2-[α-(2,3-dimethyl)-phenoxybutyl]-imidazoline are dissolved in 30 ml of methylene chloride and the solution is then saturated with HCl gas while cooling. The solvent is then stripped off and, with stirring, 100 ml of ether are added to the residue. The product is crystallised by trituration with a glass rod. The crystals are collected by filtration and dried, affording pure 2-[α-(2,3-dimethyl)-phenoxybutyl]-imidazoline hydrochloride which melts at 137°–139° C.

EXAMPLE 3: (Process e)

2-[α-(2,3-Dimethyl)-phenoxypropyl]-imidazoline 13.3 g of methyl 2-(2,3-dimethyl)-phenoxybutyrate and 21.6 g of anhydrous ethylenediamine are dissolved in 50 ml of absolute methanol and the solution is refluxed for 6 hours. The reaction mixture is cooled and the methanol is removed in vacuo. The crude product, in the form of a brown oil which soon solidifies, is stirred for 12 hours at 15 torr and 200° C. The reaction mixture becomes solid on cooling to room temperature. Recrystallisation from hexane yields 2-[α-(2,3-dimethyl)-phenoxypropyl]-imidazoline with a melting point of 90°–91° C.

Manufacture of the starting material

The procedure is analogous to that described in Example 1.

The following compounds of formula I are obtained by procedures analogous to those described in the preceding Examples:

| $R_1$ | $R_2$ | $R_3$ | Acid addition salt | Physical data |
|---|---|---|---|---|
| CH$_3$ | CH$_3$ | C$_2$H$_5$ | | m.p. 90–91° C. |
| Cl | Cl | C$_2$H$_5$ | | m.p. 112–114° C. |
| Cl | Cl | C$_2$H$_5$ | HCl | m.p. 163–164° C. |
| CH$_3$ | CH$_3$ | i-C$_3$H$_7$ | | m.p. 100–102° C. |
| CH$_3$ | Cl | C$_2$H$_5$ | | m.p. 119–120° C. |
| CH$_3$ | Cl | C$_2$H$_5$ | HCl | |
| CH$_3$ | CH$_3$ | C$_2$H$_5$ | HCl | m.p. 184–186° C. |
| CH$_3$ | CH$_3$ | C$_2$H$_5$ | HOOC—COOH | m.p. 110–118° C. |
| —(CH$_2$)$_3$— | | C$_2$H$_5$ | | m.p. 80–81° C. |
| CH$_3$ | CH$_3$ | n-C$_3$H$_7$ | | m.p. 82–84° C. |
| CH$_3$ | CH$_3$ | n-C$_3$H$_7$ | HCl | m.p. 137–139° C. |
| —(CH$_2$)$_4$— | | C$_2$H$_5$ | | m.p. 93–94° C. |
| Cl | CH$_3$ | C$_2$H$_5$ | | |
| Cl | CH$_3$ | n-C$_3$H$_7$ | | |
| Cl | CH$_3$ | i-C$_3$H$_7$ | | |
| CH$_3$ | Cl | n-C$_3$H$_7$ | | |

-continued

| R₁ | R₂ | R₃ | Acid addition salt | Physical data |
|---|---|---|---|---|
| Cl | Cl | n-C₃H₇ | | m.p. 144–145° C. |
| CH₃ | Cl | i-C₃H₇ | | |
| Cl | Cl | i-C₃H₇ | | |
| —(CH₂)₃— | | n-C₃H₇ | | |
| —(CH₂)₄— | | n-C₃H₇ | | |
| —(CH₂)₃— | | i-C₃H₇ | | |
| —(CH₂)₄— | | i-C₃H₇ | | |

EXAMPLE 4

Action against spider mites

Phaseolus vulgaris plants (dwarf beans) were infected 16 hours before the test with infested pieces of leaf from a mass culture of *Tetranychus urticae*. At the time of application, a large number of both eggs and all mobile stages are present on the plants. On a rotary table the plants infected with the mites were sprayed with about 100 ml of an aqueous emulsion preparation containing the active substance in a concentration of 800 ppm, such that the spray did not run off. The treated plants were then kept in a greenhouse compartment at about 25° C. Evaluation was made 7 days after the treatment in order to determine the percentage kill of eggs, larvae and adults. The compounds of the preceding Examples were very effective in this test.

EXAMPLE 5

Action against parasitic mites

Batches of about 50 mites in different stages (larvae, nymphs and imagines) were taken from hens infected with *Dermanyssus gallinae*. Each batch of mites were wetted in a dilution series with an aqueous emulsion, solution or suspension of the respective active substance to be tested. This was accomplished by pouring the liquid preparation containing the active substance over the batch in a test tube. The fluid was then absorbed by a cottonwool plug. The treated mites remained for 72 hours in the test tube. The minimum active substance concentration necessary for 100% kill of the treated mites was determined in comparison with untreated controls. The compounds of the preceding Examples were very effective in this test.

What is claimed is:

1. A compound of the formula

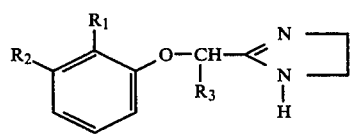

wherein R₁ and R₂, each independently of the other, are methyl or chlorine, and R₃ is ethyl or n-propyl, or an acid addition salt thereof.

2. A compound according to claim 1 of the formula

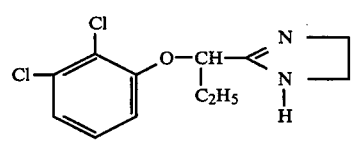

3. A compound according to claim 1 of the formula

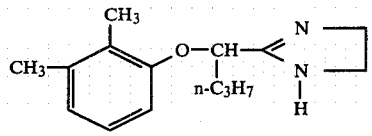

4. A compound according to claim 1 of the formula

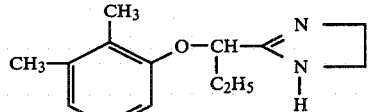

5. A compound according to claim 1 of the formula

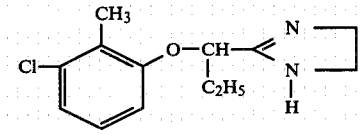

6. A compound according to claim 1 of the formula

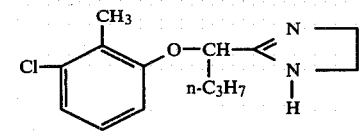

7. A compound according to claim 1 of the formula

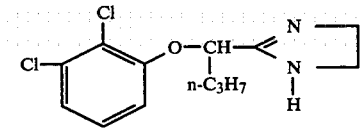

8. A compound according to claims 2, 3, 4, 5, 6 or 7 which is in the form of an acid addition salt.

9. A composition for controlling plant-damaging mites and mites which are parasites of animals, which contains, as active component, a miticidally effective amount of a compound according to claim 1 together with suitable carriers and/or other adjuvants.

10. A method of controlling plant damaging mites and mites which are parasites of animals, which comprises applying to the locus of said mites a miticidally effective amount of a compound of the formula

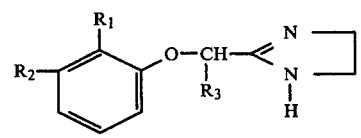

wherein R₁ and R₂, each independently of the other, are methyl or chlorine, and R₃ is ethyl or n-propyl, or an acid addition salt thereof.

11. The method according to claim 10 in which the compound is 2-[α-(2,3-dichloro)-phenoxypropyl]-imidazoline.

12. The method according to claim 10 in which the compound is 2-[α-(2,3-dimethyl)-phenoxybutyl]-imidazoline.

13. The method according to claim 10 in which the compound is 2-[α-(2,3-dimethyl)-phenoxypropyl]-imidazoline.

14. The method according to claim 10 in which the compound is 2-[α-(2-methyl-3-chloro)-phenoxypropyl]-imidazoline.

15. The method according to claim 10 in which the compound is 2-[α-(2-methyl-3-chloro)-phenoxybutyl]-imidazoline.

16. The method according to claim 10 in which the compound is 2-[α-(2,3-dichloro)-phenoxybutyl]-imidazoline.

17. A method according to claims 11, 12, 13, 14, 15 or 16 in which the compound is in the form of an acid addition salt.

* * * * *